United States Patent
Souza et al.

(10) Patent No.: US 10,576,256 B2
(45) Date of Patent: Mar. 3, 2020

(54) ANTISEPTIC APPLICATOR (71) Applicant: Becton, Dickinson and Company, Franklin Lakes, NJ (US)

(72) Inventors: Marcel A. Souza, Lehi, UT (US); Adam Zerda, Cary, NC (US); Joanne Ferranti, West Jordan, UT (US); Erik Kurt Witt, Wyckoff, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 593 days.

(21) Appl. No.: 15/377,092

(22) Filed: Dec. 13, 2016

(65) Prior Publication Data

US 2018/0161560 A1 Jun. 14, 2018

(51) Int. Cl.
| *A61F 13/40* | (2006.01) |
| *A61M 35/00* | (2006.01) |
| *A61B 90/80* | (2016.01) |
| *A61B 90/00* | (2016.01) |
| *B65D 47/42* | (2006.01) |

(52) U.S. Cl.
CPC .......... *A61M 35/006* (2013.01); *A61B 90/80* (2016.02); *A61M 35/003* (2013.01); *A61B 2090/395* (2016.02); *A61M 2205/3331* (2013.01); *A61M 2205/583* (2013.01); *B65D 47/42* (2013.01)

(58) Field of Classification Search
CPC .............. A61M 35/006; A61M 35/003; A61M 2205/3331; A61M 2205/583; A61B 90/80; A61B 2090/395; B65D 47/42
See application file for complete search history.

(56) References Cited

U.S. PATENT DOCUMENTS

| 4,925,327 A | 5/1990 | Wirt |
| 5,147,337 A | 9/1992 | Plone |
| 5,308,180 A | 5/1994 | Pournoor et al. |
| 5,435,660 A | 7/1995 | Wirt |
| 5,509,744 A | 4/1996 | Frazier |
| 5,713,843 A | 2/1998 | Vangsness |
| 6,371,675 B1 | 4/2002 | Hoang et al. |
| 6,391,014 B1 | 5/2002 | Silverman |
| 6,536,975 B1 | 3/2003 | Tufts |
| 6,729,786 B1 | 5/2004 | Tufts et al. |
| 6,846,297 B2 | 1/2005 | Lin |
| 6,916,133 B2 | 7/2005 | Hoang et al. |
| 6,991,394 B2 | 1/2006 | Tufts et al. |
| 8,348,913 B2 | 1/2013 | Hoang et al. |
| 2002/0076255 A1 | 6/2002 | Hoang |

(Continued)

FOREIGN PATENT DOCUMENTS

| JP | 2004-516078 A | 6/2004 |
| JP | 2006-520571 A | 9/2006 |

(Continued)

*Primary Examiner* — Tatyana Zalukaeva
*Assistant Examiner* — Gabriella E Burnette
(74) *Attorney, Agent, or Firm* — Kirton & McConkie; Craig Metcalf; Kevin Stinger (57) ABSTRACT

An antiseptic applicator may include a handle, a sponge, and a usage indicator. The handle may be configured to store antiseptic solution. The sponge may be configured to absorb the antiseptic solution when the antiseptic solution is released from the handle. The usage indicator may be configured to indicate a period of time that the sponge has been pressed to skin of a patient.

17 Claims, 5 Drawing Sheets

(56) References Cited

U.S. PATENT DOCUMENTS

| | | | |
|---|---|---|---|
| 2002/0076258 A1 | 6/2002 | Crosby et al. | |
| 2004/0162533 A1 | 8/2004 | Alley | |
| 2004/0240927 A1 | 12/2004 | Hoang et al. | |
| 2006/0039741 A1 | 2/2006 | Tufts et al. | |
| 2007/0269255 A1 | 11/2007 | Marcellus | |
| 2008/0154210 A1 | 6/2008 | Jordan et al. | |
| 2010/0217357 A1 | 8/2010 | Da Silva | |
| 2013/0202482 A1* | 8/2013 | Froimson | A61M 35/006 422/28 |
| 2015/0148686 A1 | 5/2015 | Baym et al. | |
| 2016/0151803 A1 | 6/2016 | Arwatz et al. | |
| 2018/0104017 A1* | 4/2018 | Heacock | A61B 90/08 |

FOREIGN PATENT DOCUMENTS

| | | |
|---|---|---|
| WO | 2009/076612 A1 | 6/2009 |
| WO | 2016/090152 | 6/2016 |

\* cited by examiner

ANTISEPTIC APPLICATOR

BACKGROUND OF THE INVENTION

The present disclosure relates generally to antiseptic applicators. Clinician practices related to cleaning skin of a patient prior to a procedure, such as, for example, an intravenous catheter insertion or surgery, may be inconsistent and may deviate from protocol and recommended guidelines. In further detail, clinicians may not clean an insertion or surgical site for a sufficient amount of time to remove unwanted bacteria prior to the insertion or the surgery. Failure to clean the insertion or surgical site for the sufficient amount of time may result in an increased likelihood of infection for the patient. For example, a patient's chances of developing a catheter-related bloodstream infection ("CRBSI") and/or surgical site infection ("SSI") may increase. CRBSIs and SSIs are responsible for increased health care costs.

Accordingly, there is a need in the art for devices and methods that facilitate cleaning of the insertion site for the sufficient amount of time. Such devices and methods are disclosed herein.

BRIEF SUMMARY OF THE INVENTION

The present disclosure relates generally to antiseptic applicators and associated methods of use. In some embodiments, the antiseptic applicator may include an antiseptic solution, which may be used to clean or sterilize skin of a patient. In some embodiments, the antiseptic solution may be used to clean the skin prior to a procedure such as, for example, intravenous catheter insertion or surgery. In some embodiments, the antiseptic solution may be disposed within a handle of the antiseptic applicator. In some embodiments, the handle may store the antiseptic solution.

In some embodiments, the antiseptic applicator may include a sponge, which may be configured to absorb the antiseptic solution when the antiseptic solution is released from the handle or another storage location. In some embodiments, the antiseptic applicator may include a usage indicator, which may be configured to indicate a length or period of time that the antiseptic applicator, and thus, the antiseptic solution, has been pressed on the skin of the patient. In some embodiments, pressing the antiseptic applicator on the skin of the patient may include scrubbing the skin with the antiseptic applicator. In further detail, in some embodiments, pressing the antiseptic applicator on the skin of the patient may include pressing a bottom portion of the sponge of the antiseptic application on the skin of the patient. In some embodiments, pressing the antiseptic applicator on the skin of the patient may include pressing the antiseptic applicator on the skin of the patient with enough force such that output from one or more pressure sensors of the antiseptic applicator meets or exceeds a threshold value.

Various types of usage indicators may be used. In some embodiments, the usage indicator may include an audible alarm or a vibrator. In some embodiments, the usage indicator may include a color-changing element. Various types of color-changing elements may be used. In some embodiments, the color-changing element may include a peelable color-changing element, which may include an outer liner that may be removed or partially removed or peeled. In response to the outer liner being partially removed or peeled, one or more chemicals of the peelable color-changing element may change color upon exposure to air for a particular amount of time. In some embodiments, the peelable color-changing element may be configured such that the change in color occurs after a predetermined period of time.

In some embodiments, a clinician may peel the outer liner of the color-changing element immediately prior to or immediately after pressing the antiseptic applicator on the skin of the patient and may continue to press the antiseptic applicator on the skin until the change in color occurs. In some embodiments, the change in color may indicate to the clinician that the clinician has pressed the antiseptic applicator to the skin of the patient for the predetermined period of time or threshold, which may correspond to improved or best practices for infection prevention. For example, the predetermined period of time may be between thirty and sixty seconds. The peelable color-changing element may be various shapes and sizes. In some embodiments, the peelable color-changing element may be configured as a strip.

In some embodiments, the color-changing element may include a reservoir of one or more chemicals. In some embodiments, the reservoir may be configured such that when the clinician presses on the reservoir, the chemicals may mix, which may cause a color of the usage indicator to change after the predetermined period of time. The clinician may press the reservoir immediately prior to or immediately after pressing the antiseptic applicator on the skin of the patient and may be able to determine when the antiseptic applicator, and thus, the antiseptic solution, has been pressed to the skin for a sufficient period of time to prevent infection.

In some embodiments, the usage indicator may include one or more lights, such as, for example, light emitting diodes ("LEDs"). In these and other embodiments, the antiseptic applicator may further include a pressure sensor portion, which may be disposed between the handle and the sponge. The pressure sensor portion may include one or more pressure sensors. In some embodiments, the one or more pressure sensors may be configured to detect pressing of the antiseptic applicator on the skin of the patient. In further detail, in some embodiments, the one or more pressure sensors may be configured to detect pressing of the sponge of the antiseptic applicator on the skin of the patient. In some embodiments, the antiseptic applicator may also include a timer, which may be electrically coupled to the usage indicator and/or the one or more pressure sensors of the pressure sensor portion. In some embodiments, the one or more pressure sensors may include the timer.

In some embodiments, the timer may be responsive to output from the one or more pressure sensors. In some embodiments, the output from the one or more pressure sensors may result from pressing the antiseptic applicator on the skin of the patient. In some embodiments, the timer may count elapsed time corresponding to a time that the antiseptic applicator is pressed to the skin of the patient. For example, the timer may start counting the elapsed time in response to any output from the one or more pressure sensors. As another example, the timer may start counting elapsed time in response to the output meeting or exceeding a threshold value. In some embodiments, the timer may stop counting the elapsed time when the output from the one or more pressure sensors stops or falls below the threshold value. In some embodiments, the timer may retain counted elapsed time when the timer stops counting the elapsed time such that when the output again meets or exceeds the threshold value, the timer may start at the counted elapsed time instead of from zero. In some embodiments, the timer may retain counted elapsed time in this manner until it is reset through any number of means, such as, for example, powering off of the antiseptic applicator or automatic resetting of the timer when a predetermined period of time or threshold has passed.

In some embodiments, when the elapsed time equals the predetermined period of time, one or more light sources may be turned on or change color to indicate to the clinician that a desired minimum cleaning duration has been achieved. In some embodiments, the light sources may include light-emitting diodes ("LEDs").

In some embodiments, the pressure sensor portion and/or the one or more pressure sensors may be generally flat or planar. In some embodiments, the handle may be coupled with the pressure sensor portion through any suitable means, such as, for example, attaching or fastening. In some embodiments, the handle may be configured to contact and/or press on the pressure sensor portion in response to the clinician holding the handle and pressing the antiseptic applicator on the skin of the patient. In some embodiments, an aperture may extend through the pressure sensor portion and/or the one or more pressure sensors. In these and other embodiments, the pressure sensor portion and/or the one or more pressure sensors may be configured generally in a loop. In some embodiments, an outer diameter of the handle may be larger than the aperture and/or approximately the same as an outer diameter of the loop.

In some embodiments, the antiseptic solution may be configured to move from the handle to the sponge through the aperture when the antiseptic solution is released from the handle. The antiseptic solution may be released from the handle through any number of mechanisms. For example, the antiseptic solution may be contained in a sealed manually crushable glass ampule protected by the handle or a flexible cover to protect a hand of a user during manual crushing of the ampule to release the antiseptic solution therefrom. In some embodiments, upon crushing of the glass ampule, the antiseptic solution may be released therefrom and impregnate the sponge, allowing the user to spread the antiseptic solution across an area to be sanitized. In some embodiments, a bottom of the handle may include a hole through which the antiseptic solution may be configured to flow at a predetermined rate. In some embodiments, the antiseptic solution may be released as described, for example, in U.S. Pat. No. 6,536,975, filed Nov. 10, 2000, or U.S. Pat. No. 5,690,958, filed Sep. 30, 1996, which are incorporated by reference herein in their entirety. In some embodiments, the antiseptic solution may be released from the handle prior to pressing of the sponge on skin of the patient and/or starting of the timer.

In some embodiments, the antiseptic applicator may include a coupler element, which may include the pressure sensor portion. In some embodiments, the aperture may extend through the pressure sensor portion and/or the coupler element. In some embodiments, the pressure sensor portion may extend along at least a portion of an edge of the aperture. In some embodiments, the coupler element may be disposed within a depression in an upper surface of the sponge. For example, the coupler element may be configured to fit snugly within the depression. In some embodiments, the one or more LEDs may be disposed on the coupler element. For example, the one or more LEDs may be disposed on an edge of the coupler element. The one or more LEDs may be disposed in various positions on the antiseptic applicator that may allow the clinician to view the one or more LEDs.

In some embodiments, the handle may be elongated. In some embodiments, the handle may be at least partially hollow, which may allow the handle to hold the antiseptic solution within the handle. In some embodiments, one or more batteries may be electrically coupled to one or more of the following: the timer, the usage indicator, and the one or more pressure sensors.

In some embodiments, the handle may include an electronic circuit board. The circuit board may include, for example, a printed circuit board. In some embodiments, the timer and/or the one or more batteries may be mounted on the circuit board. The usage indicator and/or the pressure sensor may be electrically coupled to the one or more batteries and/or the timer via the circuit board. In some embodiments, a lower edge of the circuit board may be configured to contact the pressure sensor portion to electrically couple the one or more pressure sensors to the one or more batteries and/or the timer. In some embodiments, the handle and/or the circuit board may be disposed at an angle with respect to one or more of the following: the pressure sensor portion, the coupler element, and the sponge.

In some embodiments, the antiseptic applicator may include a communication unit which may be configured to send data to a device, such as a Smart Phone, computer, or any other electronic device, via Bluetooth, Near Field Communication (NFC), Radio Frequency Identification (RFID), WiFi, or another communication technology. In some embodiments, the data may include whether or not the clinician pressed the antiseptic applicator to the skin of the patient for the predetermined period of time and/or an amount of time the clinician pressed the antiseptic applicator to the skin of the patient. Thus, cleaning practices of the clinician may be monitored for safety purposes and/or compliance.

In some embodiments, a method of using the antiseptic applicator to clean the skin of the patient may include pressing the antiseptic applicator on the skin of the patient. In some embodiments, the method may include removing the antiseptic applicator from the skin after the usage indicator indicates a period of time, for example, the predetermined period of time.

BRIEF DESCRIPTION OF THE SEVERAL VIEWS OF THE FIGURES

In order that the manner in which the above-recited and other features and advantages of the invention will be readily understood, a more particular description of the cannula capture mechanism briefly described above will be rendered by reference to specific embodiments thereof, which are illustrated in the appended Figures. Understanding that these Figures depict only typical embodiments and are not, therefore, to be considered to be limiting of its scope, the invention will be described and explained with additional specificity and detail through the use of the accompanying Figures in which.

DETAILED DESCRIPTION OF THE INVENTION

The presently preferred embodiments of the described invention will be best understood by reference to the Figures, wherein like parts are designated by like numerals throughout. It will be readily understood that the components of the present invention, as generally described and illustrated in the Figures herein, could be arranged and designed in a wide variety of different configurations. FIGS. 1-8 are not intended to limit the scope of the invention, as claimed, but is merely representative of some embodiments of the invention.

Figure 1:
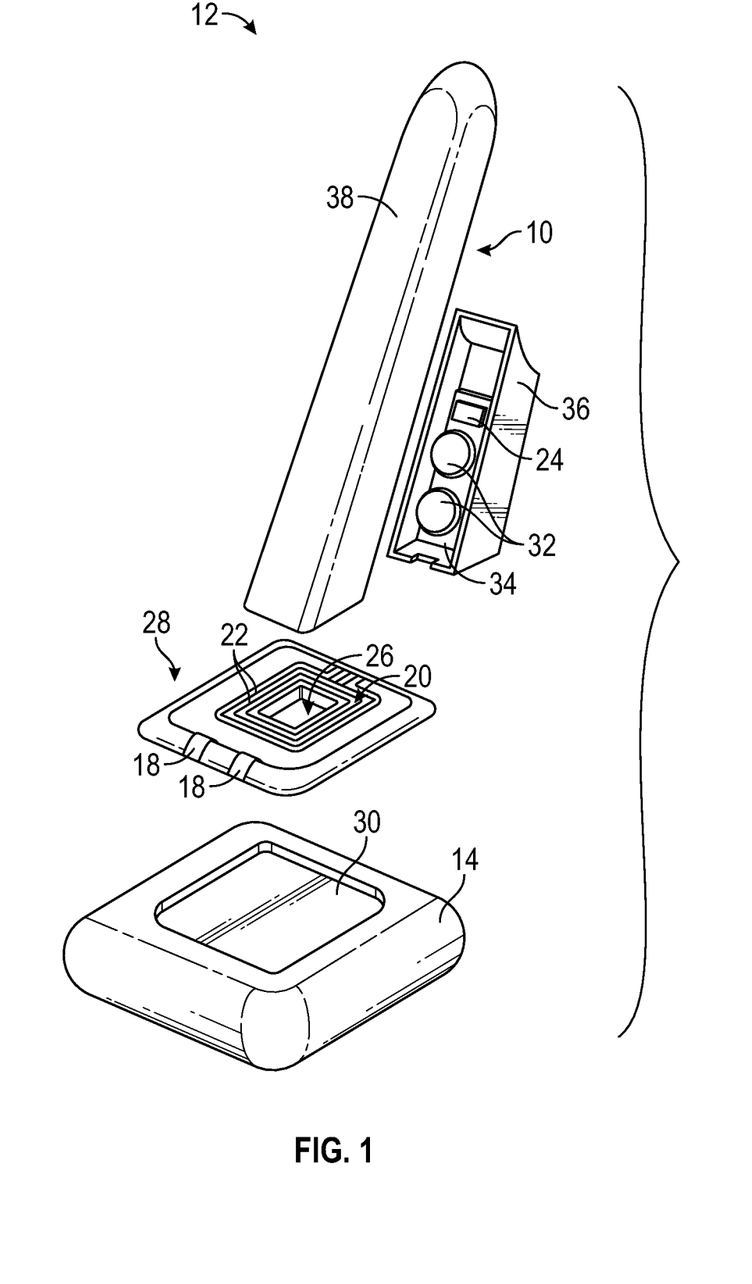
FIG. 1 is an exploded view of the antiseptic applicator of FIG. 1, according to some embodiments.

Referring now to FIG. 1, in some embodiments, antiseptic solution may be disposed within a handle 10 of an antiseptic applicator 12. In some embodiments, the handle 10 may store the antiseptic solution. In some embodiments, the antiseptic applicator 12 may be used to clean or sterilize skin of a patient. In some embodiments, the antiseptic applicator 12 may be used to clean the skin prior to a procedure such as, for example, intravenous catheter insertion.

In some embodiments, the antiseptic applicator 12 may include a sponge 14, which may be configured to absorb the antiseptic solution when the antiseptic solution is released from the handle 10. In some embodiments, the antiseptic applicator 12 may include a usage indicator, which may be configured to indicate a period of time that the antiseptic applicator 12, and thus, the antiseptic solution, has been applied or pressed to the skin of the patient.

In some embodiments, the usage indicator may include one or more lights, such as, for example, LEDs 18. In these and other embodiments, the antiseptic applicator may further include a pressure sensor portion 20, which may be disposed between the handle 10 and the sponge 14. The pressure sensor portion 20 may include one or more pressure sensors 22. In some embodiments, the one or more pressure sensors 22 may be configured to detect pressing of the antiseptic applicator 12 on the skin of the patient. In some embodiments, the antiseptic applicator 12 may also include a timer 24, which may be electrically coupled to the usage indicator and/or the one or more pressure sensors 22 of the pressure sensor portion 20. In some embodiments, the one or more pressure sensors 22 may include the timer 24.

In some embodiments, the timer 24 may be responsive to output from the one or more pressure sensors 22. In some embodiments, the output from the one or more pressure sensors 22 may result from pressing the antiseptic applicator 12 on the skin of the patient. In some embodiments, the timer 24 may count elapsed time corresponding to a time that the antiseptic applicator 12 is pressed to the skin of the patient. For example, the timer 24 may count elapsed time in response to any output from the one or more pressure sensors 22. As another example, the timer 24 may start counting the elapsed time in response to the output from the one or more pressure sensors meeting or exceeding a threshold value. The timer 24 may stop counting elapsed time when the output from the one or more pressure sensors 22 stops or falls below the threshold value. In some embodiments, the timer 24 may retain counted elapsed time when the timer 24 stops counting the elapsed time such that when the output again meets or exceeds the threshold value, the timer 24 may start at the counted elapsed time instead of from zero. In some embodiments, the timer 24 may retain counted elapsed time in this manner until it is reset through any number of means, such as, for example, powering off of the antiseptic applicator 12 or automatic resetting of the timer 24 when a predetermined period of time has passed.

In some embodiments, when the elapsed time equals a predetermined period of time, one or more particular LEDs 18 may be turned on or change color to indicate to the clinician that a desired minimum cleaning duration has been achieved. In some embodiments, when the antiseptic applicator 12 is pressed to the skin of the patient, pressure applied to the pressure sensors 22 may exceed a threshold which may result in the output and enable starting of the timer 24.

In some embodiments, a first LED 18 may be turned on in response to pressing of the antiseptic applicator 12 on the skin of the patient and output from the one or more pressure sensors 22. In some embodiments, a second LED 18 may be turned on in response to the elapsed time being equal to or greater than the predetermined period of time. In some embodiments, the predetermined period of time may correspond to a length of time to press the antiseptic applicator 12 to the skin of the patient according to improved or best practices for infection prevention. For example, the predetermined period of time may be between thirty and sixty seconds.

In some embodiments, the pressure sensor portion 20 and/or the one or more pressure sensors 22 may be generally flat. In some embodiments, the handle 10 may be coupled with the pressure sensor portion 20 through any suitable means, such as, for example, attaching or fastening. In some embodiments, the handle 10 may contact and/or cover the one or more pressure sensors 22. In some embodiments, the handle 10 may be configured to press on the pressure sensor portion 20 in response to the clinician holding the handle 10 and pressing the antiseptic applicator 12 on the skin of the patient. In some embodiments, an aperture 26 may extend through the pressure sensor portion 20 and/or the one or more pressure sensors 22. In these and other embodiments, the pressure sensor portion 20 and/or the one or more pressure sensors 22 may be configured generally in a loop. In some embodiments, an outer diameter of the handle 10 may be larger than the aperture 26 and/or approximately the same as an outer diameter of the loop.

In some embodiments, the antiseptic solution may be configured to move from the handle 10 to the sponge 14 through the aperture 26 when the antiseptic solution is released from the handle 10. The antiseptic solution may be released from the handle 10 through any number of mechanisms. For example, a bottom of the handle 10 may include a hole through which the antiseptic solution may be configured to flow at a predetermined rate.

In some embodiments, the antiseptic applicator 12 may include a coupler element 28, which may include the pressure sensor portion 20. In some embodiments, the aperture 26 may extend through the pressure sensor portion 20 and/or the coupler element 28. In some embodiments, the pressure sensor portion 20 may extend along at least a portion of an edge of the aperture 26. In some embodiments, the coupler element 28 may be disposed within a depression 30 in an upper surface of the sponge 14. For example, the coupler element 28 may be configured to fit snugly within the depression 30. In some embodiments, the one or more LEDs 18 may be disposed on the coupler element 28. For example, the one or more LEDs 18 may be disposed on an edge of the coupler element 28. The one or more LEDs 18 may be disposed in various positions on the antiseptic applicator 12 that may allow the clinician to view the one or more LEDs 18.

In some embodiments, the handle 10 may be elongated. In some embodiments, one or more batteries 32 may be electrically coupled to one or more of the following: the timer 24, the usage indicator, and the one or more pressure sensors 22.

In some embodiments, the handle 10 may include an electronic circuit board 34. The circuit board 34 may include, for example, a printed circuit board. In some embodiments, the timer 24 and/or the one or more batteries 32 may be mounted on the circuit board 34. The usage indicator and/or the one or more pressure sensors 22 may be electrically coupled to the one or more batteries 32 and/or the timer 24. In some embodiments, the usage indicator and/or the one or more pressure sensors 22 may be electrically coupled to the one or more batteries 32 and/or the timer 24 via the circuit board 34. In some embodiments, the handle 10 and/or the circuit board 34 may be disposed at an angle with respect to one or more of the following: the pressure sensor portion 20, the coupler element 28, and the sponge 14. The angle may be, for example, between twenty and eighty degrees. In some embodiments, the circuit board 34 may be disposed in a housing 36 of the handle 10 and may be separated from a body 38 of the housing 10 and the antiseptic solution by a wall of the body 38. The housing 36 may be configured according to various shapes and sizes.

Figure 2:
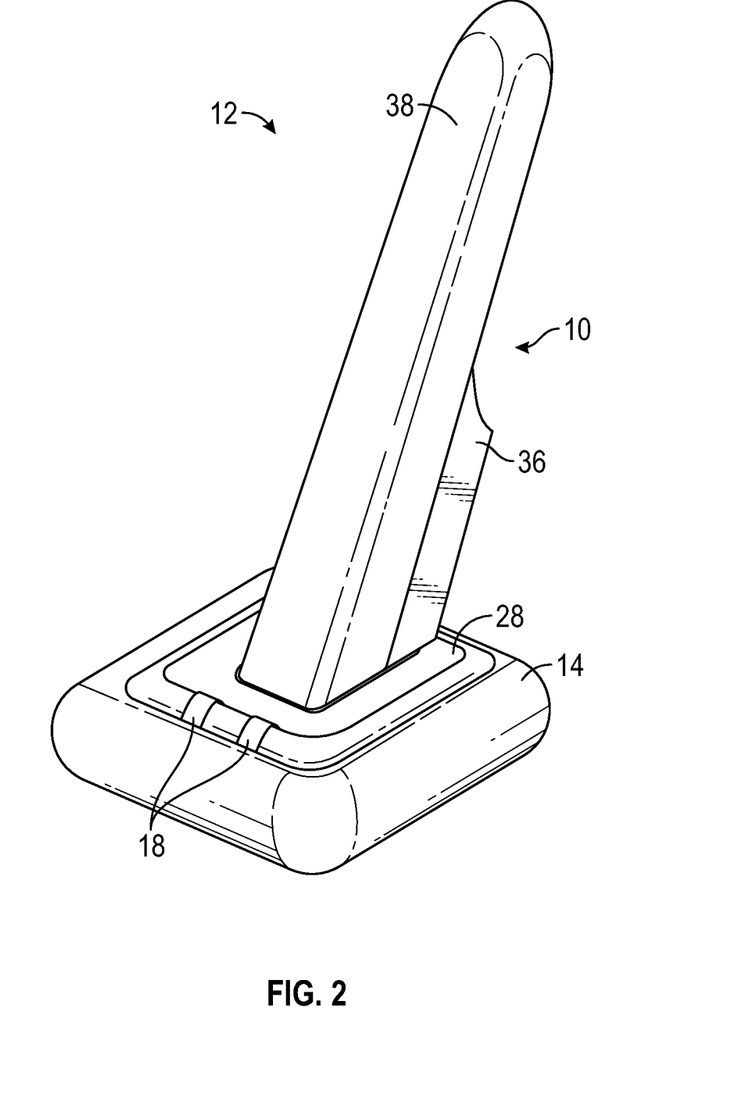
FIG. 2 is an upper perspective view of an example antiseptic applicator, according to some embodiments.
Figure 3:
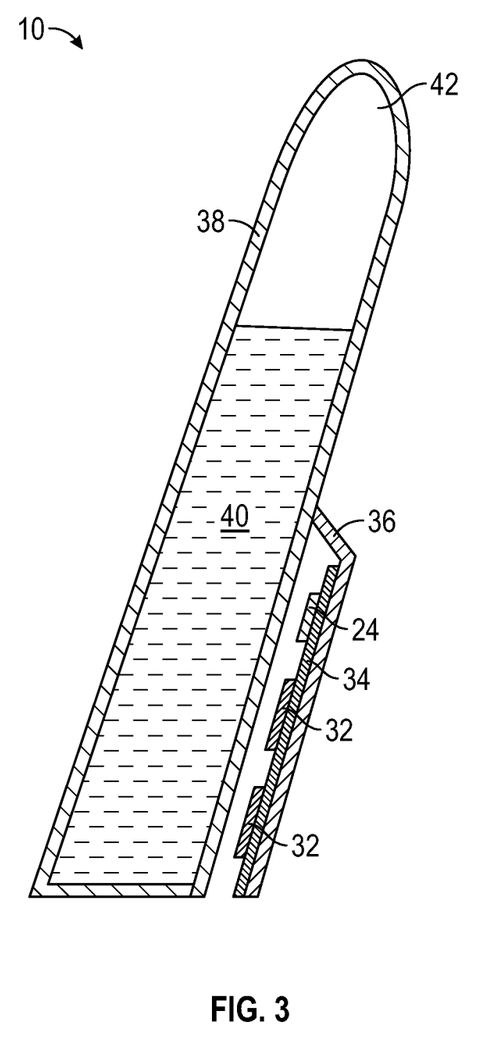
FIG. 3 is a cross-sectional view of a portion of the antiseptic applicator of FIG. 1, according to some embodiments.

Referring now to FIG. 2, the housing 36 may be coupled with the body 38 of the handle 10 through any suitable means, such as, for example, attaching or fastening. Referring now to FIG. 3, in some embodiments, the handle 10 may be at least partially hollow, which may allow the handle 10 to hold the antiseptic solution 40 within, for example, an inner lumen 42 of the body 38. In some embodiments, the inner lumen 42 may include the glass ampule. In some embodiments, the circuit board 34 may be coupled within the housing 36 of the handle 10.

Figure 4:
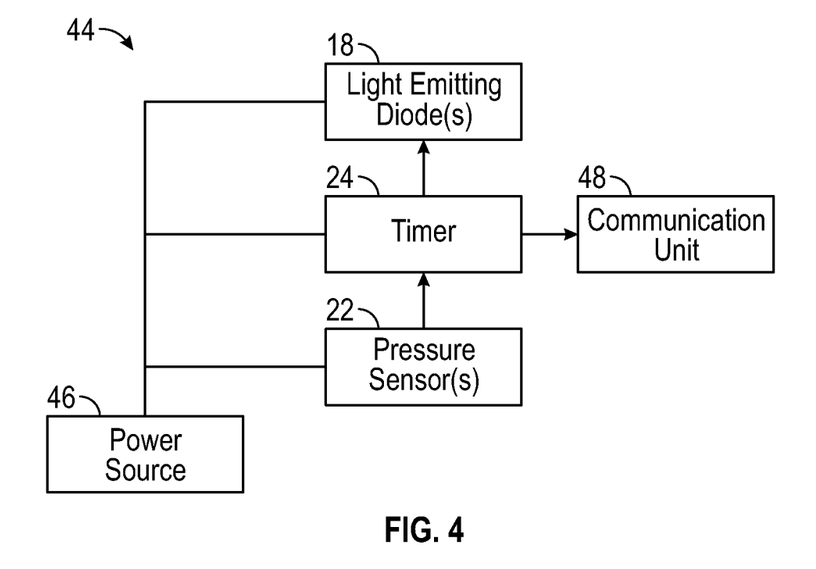
FIG. 4 is a block diagram of some circuit elements of the antiseptic applicator, according to some embodiments.

Referring now to FIG. 4, in some embodiments, circuit elements 44 of the antiseptic applicator 12 may include one or more of the following: a power source 46, the one or more LEDs 18, the timer 24, the one or more pressure sensors 22, and a communication unit 48. In some embodiments, the power source 36 may include the one or more batteries 32.

In some embodiments, the communication unit 48 may be electrically coupled with the timer 24 and may receive data from one or more of the circuit elements 44, such as, for example, the timer 24. In some embodiments, the communication unit 48 may be configured to send data to a device (not shown), such as a Smart Phone, computer, or any other device, via Bluetooth, Near Field Communication (NFC), Radio Frequency Identification (RFID), WiFi, or another communication technology. In some embodiments, the data may include whether or not the clinician pressed the antiseptic applicator 12 to the skin of the patient for the predetermined period of time and/or an amount of time the clinician pressed the antiseptic applicator 12 to the skin of the patient. Thus, cleaning practices of the clinician may be monitored for safety purposes and/or compliance.

In some embodiments, the communication unit 48 may be configured to send the amount of time the sponge has been pressed to the skin of the patient to an electronic device, which may be configured to determine that the amount of time meets the predetermined period of time or threshold. In some embodiments, the timer 24 and/or other electronics in the antiseptic applicator 12 may determine that the amount of time meets the predetermined period of time or threshold, and the communication unit 48 may send the information to the electronic device. In some embodiments, the electronic device may be configured to alert the clinician that the period of time meets the predetermined period of time. In some embodiments, the electronic device may track whether the clinician pressed the antiseptic applicator 12 to the skin of the patient for the predetermined period of time for compliance purposes. In some embodiments, in response to failure of the clinician to press the antiseptic applicator 12 to the skin of the patient for the predetermined period of time, the electronic device may indicate the failure and/or notify health care management.

A sensor or sensors of the antiseptic applicator 12 may include any sensor capable of detecting one or more of the following: the antiseptic applicator 12 is being pressed against the skin of the patient, an amount of force or pressure with which the antiseptic applicator 12 is being pressed against the skin of the patient, and whether wiping or scrubbing with the antiseptic applicator 12 is occurring. In some embodiments, the one or more pressure sensors 22 may be used in conjunction with one or more other sensors or may be replaced with the one or more other sensors. For example, the antiseptic applicator 12 may include one or more of the following: an electrical impedance sensor, a proximity sensor, an acoustic sensor, an ultrasonic sensor, and an accelerometer. In some embodiments, the one or more other sensors may be disposed within the sponge 14 and/or proximate to the sponge 14. In some embodiments, the one or more other sensors may be configured similarly to the one or more pressure sensors 22. For example, a timer may be electrically coupled to the one or more other sensors and/or the usage indicator, and the timer is configured to start counting the period of time in response to output generated by the one or more other sensors exceeding a threshold value. As another example, the one or more other sensors may include an aperture such that the antiseptic solution flows through the aperture when the antiseptic solution is released and/or may be disposed between the handle 10 and the sponge 14.

Figure 7:
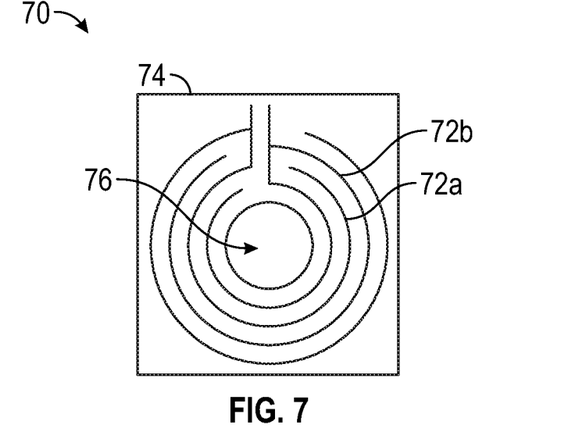
FIG. 7 is a diagram of an example electrical impedance sensor, according to some embodiments.

In some embodiments, the electrical impedance sensor may include two or more electrodes that may be arranged in various patterns or configurations on a surface of the antiseptic applicator 12 that comes in contact with the antiseptic solution 40. Referring now to FIG. 7, as an example, the electrical impedance sensor 70 may include traces 72a, 72b (referred to hereinafter as "traces 72") on a circuit board 74 that are electrical conductors. In some embodiments, in response to the antiseptic solution 40 contacting the traces 72, an electrically conductive path may be created between the traces 72 or electrodes of the circuit board 74. In some embodiments, the circuit board 74 may be disposed within and/or attached to the sponge 14 such that the antiseptic solution 40 wetting or saturating the sponge 14 may contact the circuit board 74. In some embodiments, the circuit board 74 may include the timer 24, a power source, such as the batteries 32, and/or one or more other electronics.

In some embodiments, the electrical impedance sensor 70 may include an aperture 76 that extends through the electrical impedance sensor 70. In some embodiments, the antiseptic solution may move from the handle 10, illustrated, for example, in FIGS. 1-3 and 5, to the sponge 14, also illustrated, for example, in FIGS. 1-3 and 5, through aperture 70 when the antiseptic solution is released from the handle 10.

The electrical impedance sensor may have any configuration that allows measurement of impedance and/or admittance. In some embodiments, wires embedded in the sponge 14 may directly serve as the electrodes. In some embodiments, the sponge 14 may be a conductor. Data from the one or more other sensors, such as for example, impedance data, may be transmitted to the device via the communication unit 48.

Figure 8:
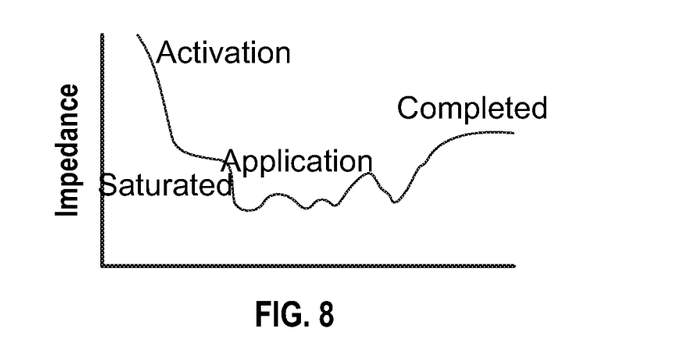
FIG. 8 is a graph of example impedance measurements corresponding to various stages of use of the antiseptic applicator, according to some embodiments.

Referring now to FIG. 8, in some embodiments, there may be five regions of impedance measurement that may be distinguished using methods such as, for example, thresholding, windowing, or complex algorithms. In some embodiments, prior to wetting of the sponge 14 and release of the antiseptic solution 40 from the handle 10 or another portion of the antiseptic applicator 12, the impedance may be determined to be high as there is little or no conductive path between the electrodes of the circuit board 74. In some embodiments, upon activation of the antiseptic applicator 12 and wetting of the sponge 14, a conductive path may be established between the electrodes and a rapid decline in impedance may be determined as more of the antiseptic solution 40 contacts the sponge 14. In some embodiments, in response to a maximum amount of the antiseptic solution 40 saturating the sponge 14, the change in impedance may slow, and the impedance may be determined to be stable. In some embodiments, as the sponge 14, which may be saturated, is applied or pressed against the patient, the conductive path through the antiseptic solution 40 may change as air may enter or leave the sponge 14. In some embodiments, when the sponge 14 is removed from the skin of the patient at completion, the sponge 14 may still have some remaining antiseptic solution 40, and the impedance may be determined to be higher than when the sponge 14 is pressed against the skin.

In some embodiments, the proximity sensor may be embedded in the sponge 14. In some embodiments, the proximity sensor may be used to measure whether the sponge 14 is in contact with the patient via capacitance, optical, thermal, or other parameters. In some embodiments, variations in the impedance and/or proximity measurements may be used to detect motion of the antiseptic applicator 12 and/or the sponge 14, which may be used to determine or estimate an amount of time the antiseptic solution 40 and/or the sponge 14 has been in contact with the patient or pressed to the skin of the patient.

In some embodiments, the acoustic and/or the ultrasonic sensor may be used to detect presence or absence of the antiseptic solution 40 in the sponge 14 and/or contact with the patient. In some embodiments, the acoustic sensor may detect release of the antiseptic solution 40 such as, for example, by detecting crushing of the glass ampule and/or release of the antiseptic solution 40 from the inner lumen 42. In some embodiments, the accelerometer may be used to measure motion of the antiseptic applicator 12 and/or the sponge 14, which may correspond to a time the antiseptic applicator 12 is pressed to the skin of the patient.

In some embodiments, the one or more pressure sensors 22 and/or the one or more other sensors may be used in conjunction with one or more switches. In some embodiments, a particular switch may include a breakable wire or other breakable electronic conductive path. In some embodiments, the particular switch may be disposed proximate to or near a storage location of the antiseptic solution 40, such as, for example, the inner lumen 42 of the handle 10. In some embodiments, release of the antiseptic solution 40 from the storage location and/or breaking the handle 10 and/or the glass ampule to allow release of the antiseptic solution 40 may facilitate breaking of the electronic conductive path, which may be detected.

Various types of usage indicators may be used. As an example, referring now to FIG. 5, the antiseptic applicator 12 may include a color-changing element 50 as the usage indicator antiseptic applicator 12. In some embodiments, the color-changing element 50 may include a peelable color-changing element 52, which may include an outer liner that may be removed or partially removed or peeled. In response to the outer liner 54 being removed or partially removed, one or more chemicals of the peelable color-changing element 52 may change color upon exposure to air for a particular amount of time. In some embodiments, the peelable color-changing element 52 may be configured such that the change in color occurs after the predetermined period of time.

Figure 5:
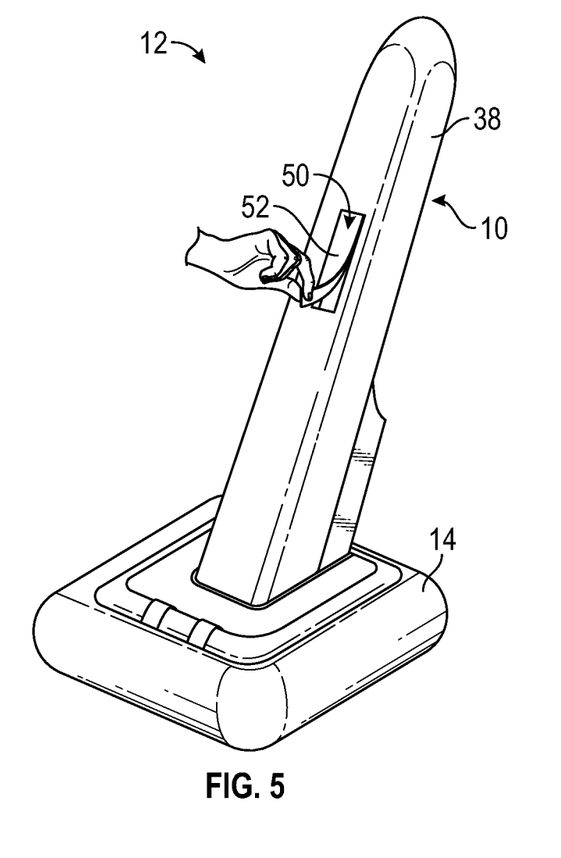
FIG. 5 is an upper perspective view of another example antiseptic applicator, according to some embodiments.

In some embodiments, the clinician may peel the outer liner 54 of the peelable color-changing element 52 immediately prior to or immediately after pressing the antiseptic applicator 12 on the skin of the patient and may continuously press the antiseptic applicator 12 on the skin until the change in color occurs. The change in color may indicate to the clinician that the clinician has pressed the antiseptic applicator 12 to the skin of the patient for the predetermined period of time. For example, the predetermined period of time may be between thirty and sixty seconds. The peelable color-changing element 52 may be various shapes and sizes. In some embodiments, the peelable color-changing element 52 may be configured as a strip, as illustrated in FIG. 5.

In some embodiments, the color-changing element 50 may include a reservoir of one or more chemicals. In some embodiments, the reservoir may be configured such that when the clinician presses on the reservoir, the chemicals may mix, which may cause a color of the usage indicator to change after the predetermined period of time. The clinician may press the reservoir immediately prior to or immediately after pressing the antiseptic applicator 12 on the skin of the patient and may be able to determine when the antiseptic applicator 12, and thus, the antiseptic solution 40 (not illustrated in FIG. 5), has been pressed to the skin for a sufficient period of time to prevent infection.

In some embodiments, the antiseptic applicator 12 may include a timer, which may be digital or analog, which may be activated by the clinician immediately prior to or immediately after pressing the antiseptic applicator 12 to the skin of the patient. In some embodiments, the timer may count the predetermined period of time, such as, for example, thirty seconds or sixty seconds. In some embodiments, the timer may include an alarm, which may sound when the predetermined period of time has elapsed. In some embodiments, the timer may be disposed in a position on the antiseptic applicator 12 that may be easily visible to the clinician, such as on an upper portion of the handle 10.

Figure 6:
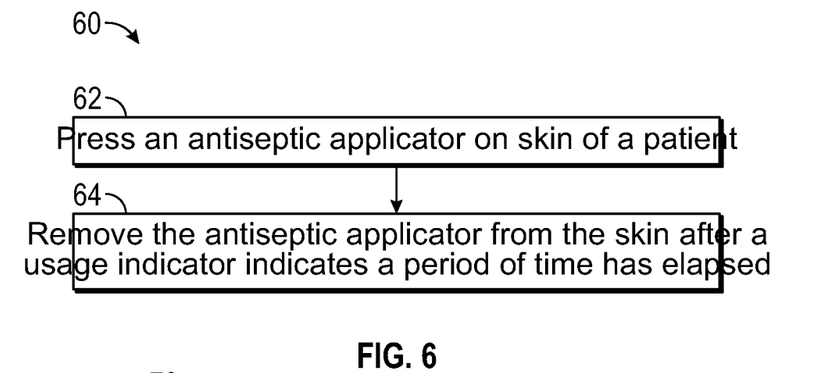
FIG. 6 is a block diagram of an example method of using an antiseptic applicator to clean skin of a patient, according to some embodiments.

FIG. 6 illustrates a block diagram of an example method 60 of using an antiseptic applicator to clean the skin of the patient, according to some embodiments. In some embodiments, the antiseptic applicator may include the antiseptic applicator 12. The method 60 may begin at block 62. At block 62, the antiseptic applicator may be pressed on the skin of the patient. In some embodiments, pressing the antiseptic applicator on the skin of the patient may also include scrubbing the antiseptic applicator on the skin of the patient. Block 62 may be followed by block 64.

At block 64, the antiseptic applicator may be removed from the skin after the usage indicator indicates a period of time has elapsed, for example, the predetermined period of time. In some embodiments, the usage indicator may include one or more LEDs, each of which may indicate the period of time by one or more of the following: changing color, turning on, and turning off. In some embodiments, the usage indicator may include a color-changing element, such as, for example, a peelable color-changing element, which may indicate the period of time by changing color.

Although illustrated as discrete blocks, various blocks may be divided into additional blocks, combined into fewer blocks, or eliminated, depending on the desired implementation. In some embodiments, the method 60 may include additional blocks. For example, in some embodiments, the method 60 may include peeling a color-changing element prior to or shortly after pressing the antiseptic applicator on the skin.

In addition to the previously described embodiments of the antiseptic applicators 12, 50, each of the antiseptic applicators 12, 50 may be modified in any suitable manner that allows it to fulfill its intended purpose. Further, the antiseptic applicators 12, 50 may be used in any suitable manner. For example, in some embodiments, the coupler element 28 may be eliminated. In these and other embodiments, the pressure sensor portion 20 illustrated in FIG. 1 may be configured to fit snugly within the depression 30 and/or the one or more LEDs 18 may be disposed on another portion of the antiseptic applicator 12, such as, for example, the handle 10, or another position.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. An antiseptic applicator, comprising:
    a handle, wherein the handle is configured to store antiseptic solution;
    a sponge configured to absorb the antiseptic solution when the antiseptic solution is released from the handle;
    a usage indicator, wherein the usage indicator is configured to indicate a period of time that the sponge has been pressed to skin of a patient;
    a pressure sensor configured to generate output in response to the sponge being pressed to the skin of the patient; and
    a timer electrically coupled to the pressure sensor and the usage indicator, wherein the timer is configured to start counting the period of time in response to the output from the pressure sensor exceeding a threshold value, wherein the output corresponds to a pressure detected by the pressure sensor.

2. The antiseptic applicator of claim 1, wherein the usage indicator includes a peelable color-changing element.

3. The antiseptic applicator of claim 1, wherein the usage indicator includes a light source.

4. The antiseptic applicator of claim 1, wherein the antiseptic solution is configured to be released from the handle prior to when the timer starts counting the period of time.

5. The antiseptic applicator of claim 1, wherein an aperture extends through the pressure sensor, wherein the antiseptic solution is configured to move from the handle to the sponge through the aperture when the antiseptic solution is released from the handle.

6. The antiseptic applicator of claim 5, wherein an outer diameter of the handle is larger than the aperture.

7. The antiseptic applicator of claim 1, wherein the pressure sensor is a pressure disposed between the handle and the sponge.

8. The antiseptic applicator of claim 1, wherein the antiseptic applicator is configured to send the period of time to an electronic device, wherein the electronic device is configured to determine that the period of time meets a predetermined threshold.

9. The antiseptic applicator of claim 1, wherein the pressure sensor includes an aperture, wherein the antiseptic solution is configured to move from the handle to the sponge through the aperture when the antiseptic solution is released from the handle.

10. The antiseptic applicator of claim 9, wherein an outer diameter of the handle is larger than the aperture.

11. The antiseptic applicator of claim 10, wherein the pressure sensor is disposed between the handle and the sponge, wherein the pressure sensor portion is generally flat.

12. The antiseptic applicator of claim 11, wherein the handle comprises an electronic circuit board, wherein the timer is disposed on the electronic circuit board, wherein the electronic circuit board is disposed at an angle with respect to the pressure sensor.

13. A method of using an antiseptic applicator to sterilize skin of a patient, the method comprising:
    pressing the antiseptic applicator on the skin of the patient, wherein the antiseptic applicator comprises:
        an antiseptic solution;
        a handle, wherein the antiseptic solution is disposed within the handle;
        a sponge, configured to absorb the antiseptic solution when the antiseptic solution is released from the handle;
        a usage indicator, wherein the usage indicator is configured to indicate a period of time that the sponge has been pressed to skin of a patient;
        a pressure sensor configured to generate output in response to the sponge being pressed to the skin of the patient; and
        a timer electrically coupled to the pressure sensor and the usage indicator, wherein the timer is configured to start counting the period of time in response to the output from the pressure sensor exceeding a threshold value, wherein the output corresponds to a pressure detected by the pressure sensor; and
    removing the antiseptic applicator from the skin of the patient after the usage indicator indicates the period of time.

14. The method of claim 13, wherein the usage indicator comprises a peelable color-changing element, further comprising peeling the color-changing element prior to pressing the antiseptic applicator on the skin of the patient.

15. The method of claim 13, wherein the usage indicator comprises a peelable color-changing element, further comprising peeling the color-changing element at a same time or shortly after pressing the antiseptic applicator on the skin of the patient.

16. The method of claim 13, wherein the usage indicator includes a light source.

17. The method of claim 13, wherein the pressure sensor portion includes an aperture, wherein the antiseptic solution is configured to move from the handle to the sponge through the aperture when the antiseptic solution is released from the handle.

* * * * *